(12) United States Patent
Chambers et al.

(10) Patent No.: US 8,956,518 B2
(45) Date of Patent: Feb. 17, 2015

(54) ELECTROCHEMICAL SENSORS WITH CARRIER FIELD

(75) Inventors: Garry Chambers, Vermont (AU); Alastair M. Hodges, Blackburn South (AU); Ronald C. Chatelier, Bayswater (AU)

(73) Assignee: LifeScan, Inc., Milpitas, CA (US)

( * ) Notice: Subject to any disclaimer, the term of this patent is extended or adjusted under 35 U.S.C. 154(b) by 285 days.

(21) Appl. No.: 13/090,620

(22) Filed: Apr. 20, 2011

(65) Prior Publication Data

US 2012/0267245 A1 Oct. 25, 2012

(51) Int. Cl.

| C12M 1/00 | (2006.01) |
|---|---|
| C12N 9/00 | (2006.01) |
| C12N 11/00 | (2006.01) |
| C25B 9/00 | (2006.01) |
| C25B 11/00 | (2006.01) |
| C25B 13/00 | (2006.01) |
| G01N 1/00 | (2006.01) |
| G01N 27/26 | (2006.01) |
| G01N 31/00 | (2006.01) |
| C12Q 1/00 | (2006.01) |
| G01N 27/327 | (2006.01) |
| A61B 5/1486 | (2006.01) |

(52) U.S. Cl.
CPC .......... *G01N 27/3272* (2013.01); *A61B 5/1486* (2013.01)
USPC ............................... 204/403.04; 204/403.02

(58) Field of Classification Search
USPC ........................ 204/403.02, 403.04
See application file for complete search history.

(56) References Cited

U.S. PATENT DOCUMENTS

| 5,437,999 A | 8/1995 | Diebold et al. |
|---|---|---|
| 5,494,562 A | 2/1996 | Maley et al. |
| 5,585,273 A | 12/1996 | Lawrence et al. |
| 5,747,351 A | 5/1998 | Hemmati |
| 5,779,867 A | 7/1998 | Shieh |
| 6,054,039 A | 4/2000 | Shieh |
| 6,284,125 B1 | 9/2001 | Hodges et al. |
| 6,326,214 B1 | 12/2001 | Liu et al. |
| 6,913,668 B2 | 7/2005 | Matzinger |
| 7,063,774 B2 | 6/2006 | Bhullar et al. |
| 7,081,188 B1 | 7/2006 | Cho |
| 7,223,248 B2 | 5/2007 | Erickson et al. |
| 7,413,640 B2 | 8/2008 | Cho |
| 7,419,821 B2 | 9/2008 | Davis et al. |

(Continued)

FOREIGN PATENT DOCUMENTS

| JP | 07-113784 | 5/1995 |
|---|---|---|
| JP | 2009-063324 | 3/2009 |

(Continued)

OTHER PUBLICATIONS

International Search Report/Written Opinion (ISR/WO); Jan. 15, 2013; 15 pages.

(Continued)

*Primary Examiner* — Luan Van
*Assistant Examiner* — Louis Rufo
(74) *Attorney, Agent, or Firm* — Hiscock & Barclay, LLP

(57) ABSTRACT

An electrochemical sensing apparatus and methods are provided. In one embodiment, an apparatus is provided having a carrier that supports an electrochemical module and that communicates between electrodes on the electrochemical module and an analyte measurement device.

23 Claims, 8 Drawing Sheets

(56) References Cited

U.S. PATENT DOCUMENTS

| | | |
|---|---|---|
| 7,455,756 B2 | 11/2008 | Choi et al. |
| 7,488,450 B2 | 2/2009 | Matusewicz et al. |
| 7,563,588 B2 | 7/2009 | Gao et al. |
| 7,713,406 B2 | 5/2010 | Gotoh et al. |
| 7,740,581 B2 | 6/2010 | Buse et al. |
| 7,758,744 B2 | 7/2010 | Zweig |
| 7,815,579 B2 | 10/2010 | Roe |
| 7,866,026 B1 | 1/2011 | Wang et al. |
| 2002/0110486 A1 | 8/2002 | Shartle et al. |
| 2003/0024811 A1 | 2/2003 | Davies et al. |
| 2005/0252784 A1 | 11/2005 | Choban et al. |
| 2006/0201804 A1 | 9/2006 | Chambers et al. |
| 2006/0254932 A1 | 11/2006 | Hodges et al. |
| 2006/0266644 A1* | 11/2006 | Pugh et al. .......... 204/400 |
| 2007/0000776 A1 | 1/2007 | Karube et al. |
| 2007/0023285 A1 | 2/2007 | Yang et al. |
| 2007/0205103 A1 | 9/2007 | Hodges et al. |
| 2008/0112848 A1 | 5/2008 | Huffstodt et al. |
| 2008/0223732 A1 | 9/2008 | Hodges et al. |
| 2009/0014328 A1* | 1/2009 | Feldman et al. ...... 204/403.02 |
| 2009/0084687 A1 | 4/2009 | Chatelier et al. |
| 2009/0093695 A1 | 4/2009 | Nakamura et al. |
| 2009/0221011 A1 | 9/2009 | Stiene et al. |
| 2009/0227898 A1 | 9/2009 | Haar et al. |
| 2009/0260986 A1* | 10/2009 | Wang et al. .......... 204/403.04 |
| 2009/0305431 A1 | 12/2009 | Hodges et al. |
| 2010/0006452 A1 | 1/2010 | Hodges et al. |
| 2010/0078322 A1 | 4/2010 | Yamanishi et al. |
| 2011/0011752 A1 | 1/2011 | Chatelier et al. |

FOREIGN PATENT DOCUMENTS

| | | |
|---|---|---|
| WO | 2009015292 A1 | 1/2009 |
| WO | 2010119341 A1 | 10/2010 |

OTHER PUBLICATIONS

Australian Examination Report for AU 2012246056; dated Sep. 2, 2014; 3 pages.

Chinese Office Action for CN 201280019188-3; dated Aug. 27, 2014; 4 pages.

Australian Examination Report for AU 2012246056; dated Oct. 20, 2014; 3 pages.

* cited by examiner

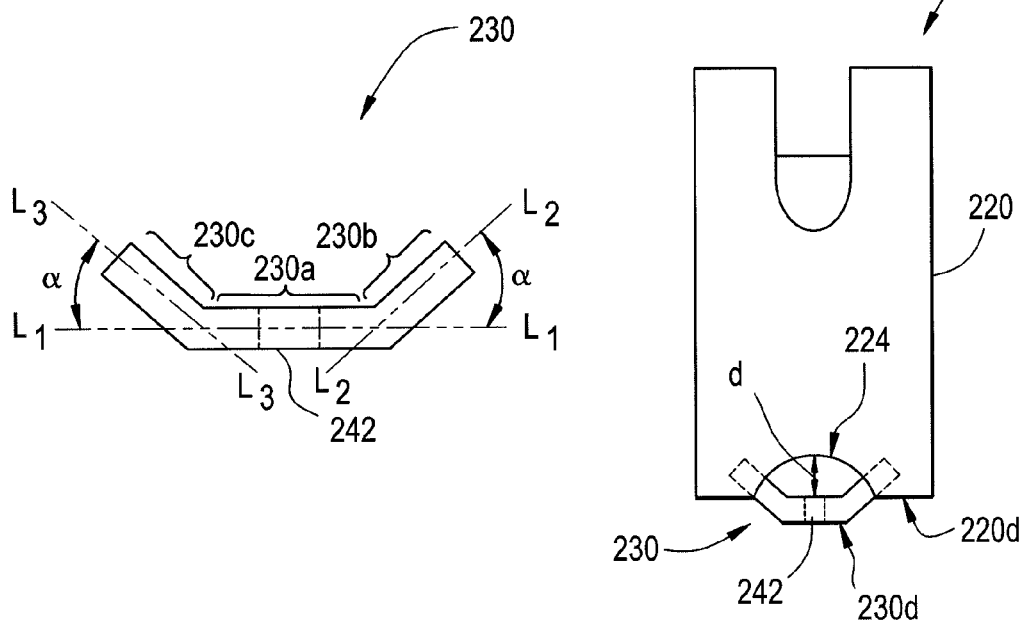
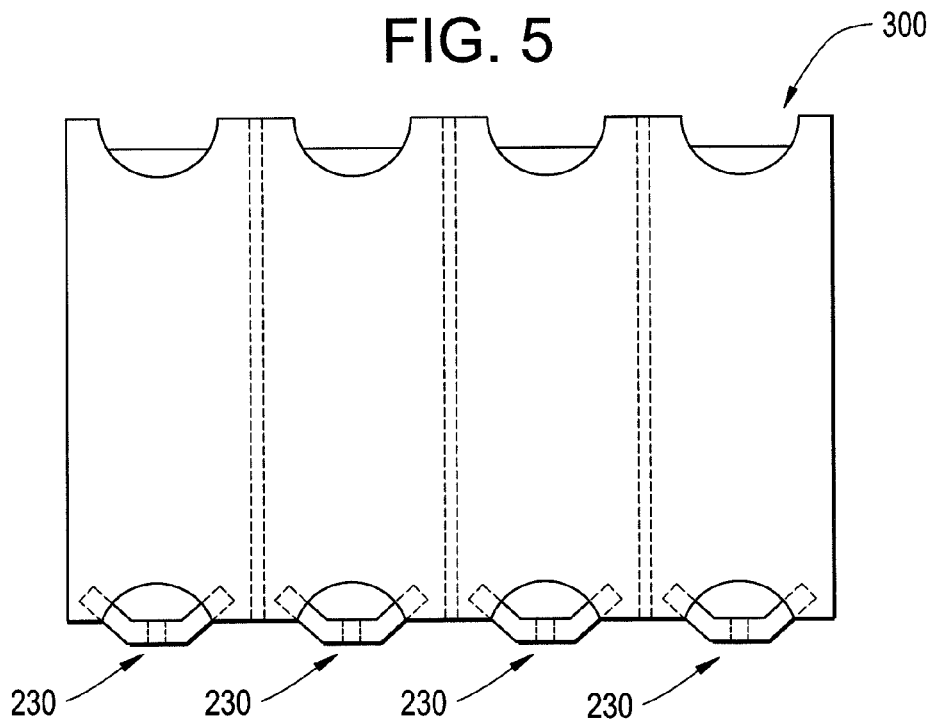

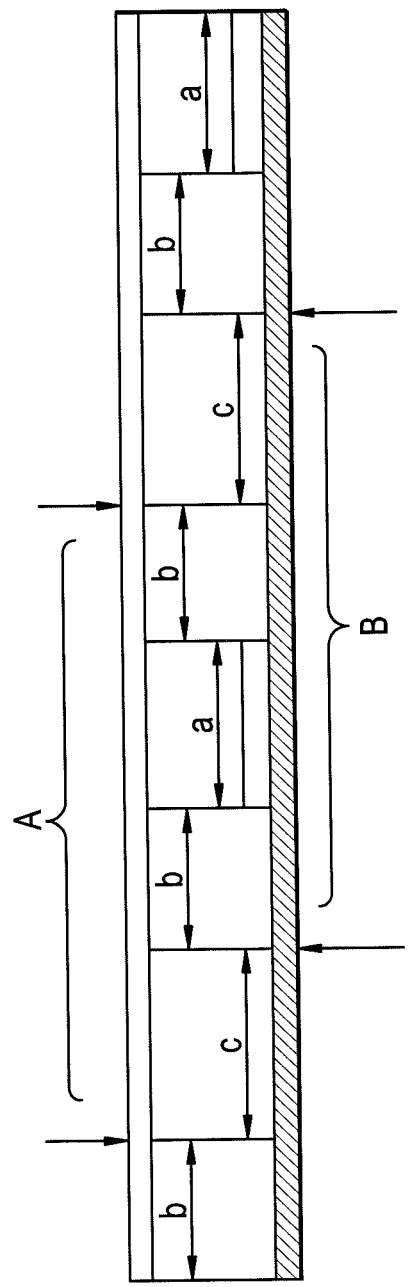

ELECTROCHEMICAL SENSORS WITH CARRIER FIELD

FIELD

The present disclosure relates to methods and systems for determining analyte concentration of a sample.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes two electrodes, e.g., a counter and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

The electrochemical cell is typically present on a test strip which is configured to electrically connect the cell to an analyte measurement device. While current test strips are effective, the size of the test strips can directly impact the manufacturing costs. While it is desirable to provide test strips having a size that facilitates handling of the strip, increases in size will tend to increase manufacturing costs where there is an increased amount of material used to form the strip. Moreover, increasing the size of the test strip tends to decrease the quantity of strips produced per batch, thereby further increasing manufacturing costs.

Accordingly, there is a need for improved electrochemical sensing apparatus and methods.

SUMMARY

The present invention generally provides electrochemical sensing apparatus and methods. In one embodiment, an electrochemical sensing apparatus is provided and includes a carrier having first and second electrically conductive regions that are electrically isolated from one another. The carrier can also include an opening extending therethrough. The apparatus also includes an electrochemical module mounted between the top and bottom portions of the carrier such that at least a portion of the electrochemical module extends across the opening. The electrochemical module includes an electrochemical cavity with a first electrode in electrical communication with the first conductive region of the carrier, a second electrode in electrical communication with the second conductive region of the carrier, and a sample receiving chamber that includes a reagent layer.

While the carrier can have a variety of configurations, in one embodiment the carrier has a top portion carrying the first conductive region, and a bottom portion carrying the second conductive region in facing relationship with the first conductive region. The carrier can be folded along a fold line to define the top and bottoms portions. The opening can be located anywhere on the carrier, but in an exemplary embodiment the opening extends across the fold line and through the first and second conductive regions. Further, the opening can be located on a distal end of the carrier, and a proximal end of the carrier can include first and second contacts configured to establish a connection between the first and second electrodes and a separate analyte measurement device. The carrier can also include an adhesive disposed between the top and bottom portions of the carrier. The adhesive can be configured to maintain the top and bottom portions at a fixed distance apart from one another and optionally to help to hold the electrochemical module in place on the carrier.

The electrochemical module can also have a variety of configurations. In one embodiment, the electrochemical module has a maximum length and a maximum width that is less than a maximum length and a maximum width of the carrier. In another embodiment, the electrochemical module can have opposed ends engaged between the top and bottom portions of the carrier, and the sample receiving chamber can be located between the opposed ends and spaced a distance apart from the carrier. A sample inlet can be located in the mid-portion of the electrochemical module such that the inlet is positioned outwardly from the opening in the carrier. In an exemplary embodiment, the electrochemical module includes a top insulating substrate carrying the first electrode, a bottom insulating substrate carrying the second electrode, and a spacer disposed between the first and second electrodes and maintaining the first and second electrodes in a spaced apart relationship with one another. The top and bottom insulating substrates can be offset from one another such that a portion of the first electrode on the top insulating substrate is in contact with the first conductive region on the carrier, and a portion of the second electrode on the bottom insulating substrate is in contact with the second conductive region on the carrier. In other aspects, the electrochemical module can be non-rectangular and can have a central portion extending along a central axis and containing the electrochemical cavity, and opposed end portions that extend angularly from the central portion such that each end portion has a central axis that extends at an angle relative to the central axis of the central portion.

In another embodiment, an electrochemical sensing apparatus is provided and includes a carrier having a first conductive area and a second conductive area that is electrically isolated from the first conductive area, and an opening formed through the carrier. The apparatus also includes an electrochemical module mounted on the carrier such that at least a portion of the module is accessible through the opening in the carrier. The electrochemical module can have a first insulating substrate carrying a first electrode in communication with the first conductive area of the carrier, and a second insulating substrate carrying a second electrode in communication with the second conductive area of the carrier. The first and second electrodes can be facing one another in a spaced apart relationship. Alternatively, the electrochemical module can have an insulating substrate carrying both the first and second electrodes positioned adjacent to one another on the same plane. The electrodes can further be offset from one another. The module can also include an electrochemical cavity for receiving a fluid sample. The electrochemical cavity can be formed between or covering the first and second electrodes. The module further includes a reagent disposed within the electrochemical cavity and on at least one of the first and second electrodes for reacting with an analyte of a fluid sample received in the electrochemical cavity.

In one embodiment the carrier has a maximum length and maximum width that is greater than a maximum length and maximum width of the electrochemical module. While the configuration of the carrier can vary, in certain aspects the carrier can be folded along a fold line to define a top portion carrying the first conductive area and a bottom portion carrying the second conductive area. The first and second conductive regions on the carrier can be electrically isolated from one another along the fold line, and optionally between the fold line and the electrochemical module. The opening in the carrier can be located at various locations, for example, along a perimeter of the carrier, and more particularly along the fold line. The carrier can also include an adhesive disposed between the top and bottom portions of the carrier and configured to maintain the top and bottom portions at a fixed distance apart from one another. Optionally, the adhesive can help to hold the electrochemical module in place on the carrier.

In other aspects, the electrochemical module can be located on a distal end of the carrier, and a proximal end of the carrier can include first and second contacts configured to establish an electrical connection between the first and second electrodes and an analyte measurement device. The electrochemical module can also include opposed ends mounted on the carrier, and a mid-portion located between the opposed ends and spaced a distance apart from the carrier. In one embodiment, the electrochemical module has a central portion extending along a central axis and containing the electrochemical cavity, and opposed end portions having central axes that extend at an angle relative to the central axis of the central portion.

In another embodiment, an electrochemical sensor apparatus is provided that includes an electrochemical module having an electrochemical cavity with first and second electrodes, and a sample receiving chamber having a reagent layer configured to react with an analyte of a fluid sample received in the electrochemical cavity. The apparatus also includes a carrier having a top insulating substrate with a first conductive region, and a bottom insulating substrate with a second conductive region. A distal cut-out extends through a distal end of the top and bottom insulating substrates, and at least a portion of the electrochemical module extends across the distal cut-out such that the first electrode is in electrical communication with the first conductive region and the second electrode is in electrical communication with the second conductive region. A proximal cut-out extends through a proximal end of the bottom insulating substrate to expose a contact area on the first conductive region of the top insulating substrate such that the first contact area and a second contact area on the bottom insulating substrate are exposed to allow electrical connection with an analyte measurement device to establish a connection between the first and second electrodes and the analyte measurement device.

In yet another embodiment, an electrochemical module is provided having a first insulating substrate carrying a first electrode and a second insulating substrate carrying a second electrode. The first and second insulating substrates can each have opposed sidewalls extending between first and second terminal ends, and an axis extending between the first and second terminal ends, and the first and second insulating substrates can be offset from one another such that a first terminal end of the first insulating substrate extends a distance beyond a first terminal end of the second insulating substrate to expose the first electrode, and a second terminal end of the second insulating substrate extends a distance beyond a second terminal end of the first insulating substrate to expose the second electrode. The first and second insulating substrates can each have a width extending between the first and second terminal ends that is at least twice a length extending between the opposed sidewalls. The module can also include at least one spacer disposed between the first and second insulating substrates and maintaining the first and second electrodes in a spaced apart relationship with one another, and an electrochemical cavity formed between the first and second electrodes and configured to receive a fluid sample. The electrochemical cavity can include a reagent configured to react with an analyte of a fluid sample received in the electrochemical cavity. In one embodiment, the at least one spacer can include a first spacer positioned adjacent to the first terminal end of the second insulating substrate, and a second spacer positioned adjacent to the second terminal end of the first insulating substrate.

In yet another embodiment, a carrier web is provided having a carrier with a longitudinally extending fold line defining a top portion having a first conductive area and a bottom portion having a second conductive area electrically isolated from the first conductive area, and a plurality of openings spaced a distance apart from one another and disposed across the fold line. The carrier web also includes a plurality of electrochemical modules, each module being mounted across one of the plurality of openings, and each electrochemical module having a first electrode in communication with the first conductive area of the carrier, a second electrode isolated from the first electrode and in communication with the second conductive area of the carrier, and an electrochemical cavity accessible through the opening in the carrier for receiving a fluid sample.

In another embodiment, a method for manufacturing an electrochemical sensing apparatus is provided and includes positioning opposed ends of an electrochemical module on a carrier such that an electrochemical cavity formed in the electrochemical module is positioned across an opening formed in the carrier, and folding the carrier to engage the opposed ends of the electrochemical module between top and bottom portions of the carrier. The electrochemical module can include a first insulating substrate carrying a first electrode that is positioned in electrical contact with a first electrically conductive region on the carrier, and a second insulating substrate carrying a second electrode that is positioned in electrical contact with a second electrically conductive region on the carrier. The method can also include, prior to positioning, forming first and second electrically conductive regions on the carrier such that the first and second electrically conductive regions are electrically isolated from one another. When the carrier is folded, the first electrically conductive region can be on the top portion of the carrier and the second electrically conductive region can be on the bottom portion of the carrier. The method can also include, prior to folding, positioning a spacer on the carrier such that the spacer maintains the top and bottom portions at a distance apart from one another when the carrier is folded.

BRIEF DESCRIPTION OF THE DRAWINGS

The present disclosure will be more fully understood from the following detailed description taken in conjunction with the accompanying drawings, in which:

FIG. 4A is a top view of another embodiment of an ECM;

FIG. 4B is a top view shown the ECM of FIG. 4A mounted onto a carrier, shown in a folded configuration, to form another embodiment of a test strip assembly;

FIG. 5 is a top view of a test strip assembly web, showing multiple test strip assemblies having a configuration as shown in FIG. 4B;

FIG. 8 is a side view of a strip of electrochemical modules.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

The present invention generally provides an electrochemical sensing apparatus having a carrier that supports an electrochemical module, and that communicates between electrodes on the electrochemical module and an analyte measurement device. The carrier is particularly advantageous as it allows the electrochemical module to have a relatively small size, while providing a large surface area for ease of handling. The small size of the electrochemical module can reduce manufacturing costs, as less material is required to form the electrodes. The carrier also provides flexibility in design, allowing for various placement of one or more electrochemical modules, as well as allowing multiple sensing apparatus to be formed as a unit.

Figure 1A:
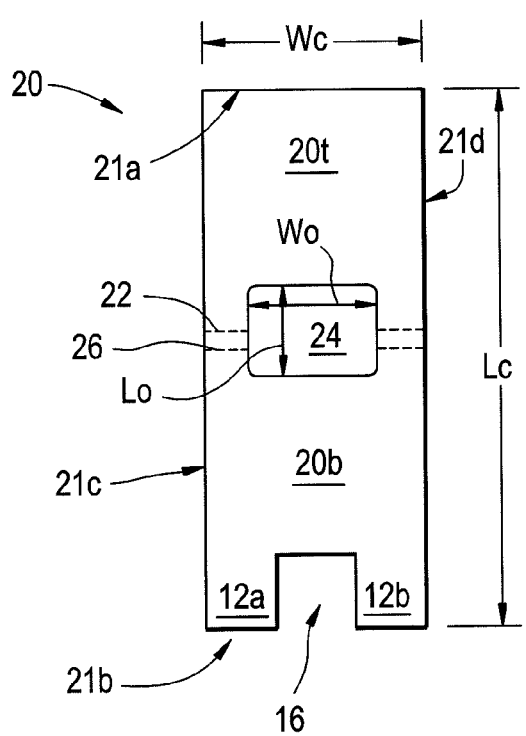
FIG. 1A is a top view of a carrier in an unfolded configuration.
Figure 1B:
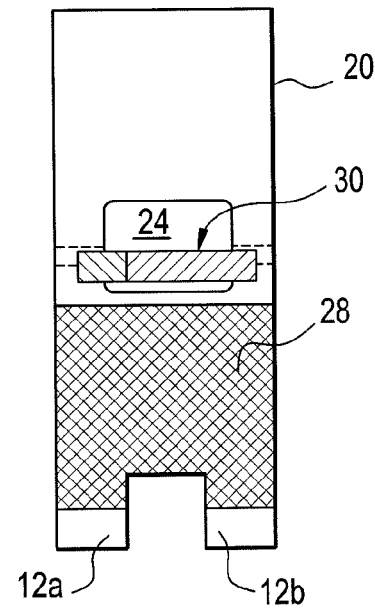
FIG. 1B is a top view of the carrier of FIG. 1A having an adhesive and an electrochemical module ("ECM") disposed thereon.
Figure 1C:
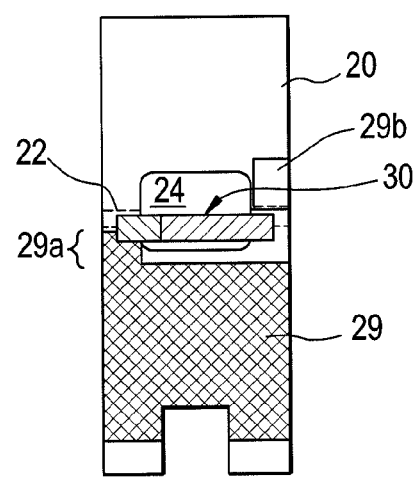
FIG. 1C is a top view of the carrier of FIG. 1A having another embodiment of an adhesive with an ECM disposed thereon.
Figure 1D:
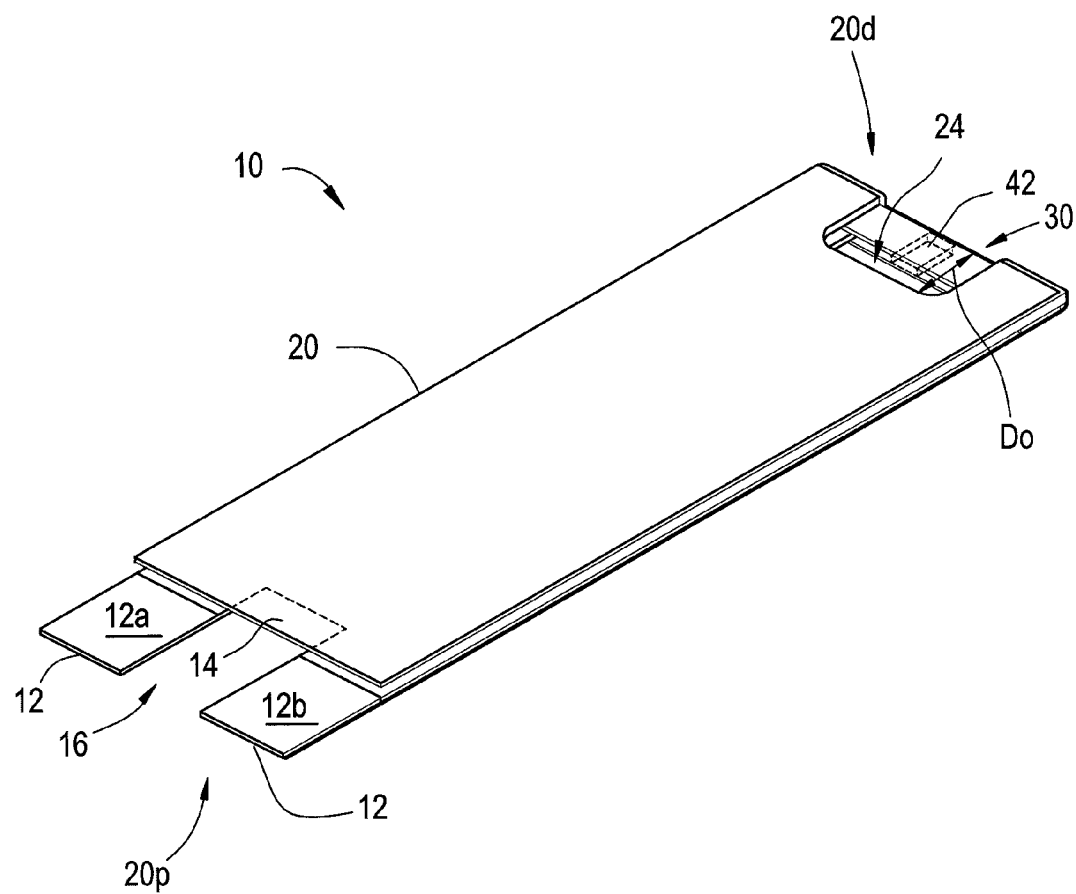
FIG. 1D is a perspective view of the carrier and ECM of FIG. 1B, shown in a folded configuration to form a test strip assembly.

FIGS. 1A-1D illustrate one exemplary embodiment of an electrochemical sensing apparatus, also referred to herein as a test strip assembly. As shown, the test strip assembly 10 generally includes a carrier 20, shown in FIG. 1A, and an electrochemical module 30 that is mounted on the carrier 20, as shown in FIGS. 1B-1D. In general, the carrier 20 has dimensions that are greater than the module 30, such that the carrier 20 serves as a support to facilitate handling of the module 30. A person skilled in the art will appreciate that the test strip assembly 10 can have various configurations other than those shown, and can include any combination of features disclosed herein and known in the art. Moreover, each test strip assembly can include any number of electrochemical modules at various locations on the carrier for measuring the same and/or different analytes in a fluid sample.

Carrier

As indicated above, FIG. 1A illustrates one embodiment of a carrier 20. The carrier 20 can have various configurations, but it is typically in the form of one or more rigid or semi-rigid substrates having sufficient structural integrity to support the electrochemical module 30 and to allow handling and connection to an analyte measurement device, as will be discussed in further detail below. The carrier can be formed from various materials, including plastic or cardboard materials. In an exemplary embodiment, materials that do not shed or that exhibit relatively low shedding of fibers are preferred. The substrate material typically is one that is non-conductive. The carrier material can also have any thermal coefficient of expansion, including a low thermal coefficient of expansion, as changes in the volume of the material during use will not have any effect on performance. In addition, the carrier materials can be inert and/or electrochemically non-functional, where they do not readily corrode over time nor chemically react with ECM material. The conductive material disposed on the carrier should be resistant to corrosion where the conductivity does not change during storage of the strip assemblies.

The shape of the carrier 20 can also vary. In the embodiment shown in FIG. 1A, the carrier 20 has a generally elongate rectangular shape with a length $L_c$ that is greater than a width $W_c$, the dimensions of which are discussed in further detail below. The carrier 20 includes first and second terminal ends 21a, 21b, and first and second opposed sidewalls 21c, 21d extending between the first and second terminal ends 21a, 21b. The carrier 20 can be formed from separate top and bottom portions, or as shown the carrier 20 can be configured to be folded along a fold line 22 to define top and bottom portions 20t, 20b that are in facing relationship with one another. A person skilled in the art will appreciate that the terms "top" and "bottom" as used herein are intended to serve as a reference for illustration purposes only, and that the actual position of the portions of the carrier will depend on the orientation of the carrier. The top and bottom portions 20t, 20b of the carrier 20 can allow an electrochemical module, e.g., module 30, to be mounted and engaged therebetween. The location of the fold line 22 can vary. In the illustrated embodiment, the fold line 22 is located offset from a mid-line of the carrier 20 to allow one of the top and bottom portions 20t, 20b of the carrier, e.g., the bottom portion 20b in FIG. 1A, to extend a distance beyond the terminal end of the other portion of the carrier 20, e.g., the top portion 20t in FIG. 1A. Such a configuration facilitates connection to an analyte measurement device, as will be discussed further below. The carrier 20 can also optionally include one or more additional fold lines, which may facilitate spaced apart positioning of the top and bottom portions 20t, 20b, as is also discussed further below. The non-conducting substrate of the carrier can be kiss-cut at the intended fold line in order to facilitate folding. If a sharp blade is used to kiss-cut the substrate, sharp edges may results, in which case it may be preferable to firmly scribe a groove in the substrate using a blunt tool. This will push aside the material of the substrate into smooth "banks"

on either side of the groove in such a way that the folded carrier will not have sharp edges.

As further shown in FIG. 1A, the carrier 20 can also include at least one hole or opening extending therethrough for providing access to the electrochemical module, as discussed further below. The quantity of openings and the location of each opening can vary depending on the intended use, for example, whether more than one module will be present in a carrier. In the illustrated embodiment, the carrier 20 has a single opening 24 located symmetrically across the fold line 22. Such a configuration will allow the opening 24 to be positioned along a perimeter of the carrier 20 when the carrier 20 is folded, as shown in FIG. 1D. While not shown, the opening 24 can alternatively be positioned along any edge (e.g., along one of the terminal ends 21a, 21b and/or the opposed sidewalls 21c, 21d) of the carrier 20, with corresponding openings extending through each of the top and bottom portions 20t, 20b. In other embodiments, the opening can extend through a mid-portion of the top and bottom portions 20t, 20b of the carrier 20 at a distance spaced apart from the perimeter or outer edge of the carrier 20.

The carrier 20 also includes one or more electrically conducting layers to facilitate communication between electrodes on the electrochemical module, discussed below, and an analyte measurement device. The electrically conducting layer(s) can be formed from any conductive material, including inexpensive materials, such as aluminum, carbon, grapheme, graphite, silver ink, tin oxide, indium oxide, copper, nickel, chromium and alloys thereof, and combinations thereof. However, precious metals that are conductive, such as palladium, platinum, indium tin oxide or gold, can optionally be used. The electrically conducting layer(s) can be disposed on all or portions of the carrier, but the particular location(s) of the electrically conducting layer(s) should be configured to electrically couple the electrochemical module to the analyte measurement device. In an exemplary embodiment, the entire portion or a substantial portion of the inwardly facing surface (i.e., the surface shown in FIG. 1A) of the carrier 20 is coated with the electrically conducting layer (not shown). As a result, each of the top and bottom portions 20t, 20b of the carrier 20 includes an electrically conducting layer disposed thereon. The carrier 20 can also include one or more electrical isolation lines, e.g., referred to herein as "breaks," formed in the electrically conducting layer to separate the layer into a first electrically conducting layer and a second electrically conducting layer that is isolated from the first electrically conducting layer. The break(s) can be formed using various techniques known in the art, such as laser etching. If the electrically conducting layer is formed by printing an ink, then an unprinted area between the top and bottom portions 20t, 20b will constitute a break. The location of the break(s) can vary. For example, the break(s) can extend along the fold line 22 such that the top portion 20t includes the first electrically conducting layer which is electrically isolated from the second electrically conducting layer on the bottom portion 20b. Thus, when the carrier 20 is folded, as shown in FIG. 1D, the first electrically conducting layer (not shown) will be positioned on an inwardly facing surface of the top portion 20t of the carrier 20, and the second electrically conducting layer (not shown) will be positioned on an inwardly facing surface of the bottom portion 20b of the carrier 20 such that the first and second electrically conducting layers are in facing relationship with one another. As shown in FIG. 1A, the electrically conducting layer includes a first break formed along the fold line 22, and a second break 26 spaced a distance apart from the first break (fold line 22). The breaks can be positioned at various locations relative to the fold line 22, including on the same or opposite sides of the fold line 22. A person skilled in the art will appreciate that carrier 20 can be manufactured to include separate electrically conducting layers, rather than forming a single layer with one or more breaks. The separate layers can be formed from the same or different materials.

In another embodiment, the electrically conducting layers can be configured to prevent "auto-starting" of the assays when one or both sidewalls 21c, 21d of the test strip are contaminated, e.g., with a salty solution such as perspiration from a user's fingers. For example, the electrically conducting layers can be formed by printing electrically conductive inks (e.g., carbon, silver, grapheme, etc.), and the material can terminate at a distance (e.g., 1 mm) from the sidewalls 21c, 21d. Such a configuration will prevent contact between the electrically conducting material and a user's fingers when they grasp the test strip.

The electrically conducting layers can also be configured enable a meter to distinguish between different types of strips (e.g., to measure different analytes in a liquid sample such as glucose, lactate, cholesterol, hemoglobin, etc.). For example, two narrow highly conducting layers (e.g., printed with silver ink) can extend down from tabs 12a, 12b towards the electrochemical cavity, with a gap between the two narrow highly conducting layers. A layer of less conducting material (e.g., printed with carbon ink) can connect the two narrow highly conducting layers. When the resistance between the tabs 12a, 12b is measured, the resistance value will be dominated by the properties of the layer of less conducting material. By varying the thickness, width etc. of the layer of less conducting material, it will be possible for the meter to distinguish between different types of strips.

In order to maintain electrical separation between the first and second electrically conductive areas when the carrier 20 is folded, the carrier 20 can further include a spacer layer, which can be an adhesive layer. The spacer layer can function to maintain the top and bottom portions 20t, 20b of the carrier 20 at a distance apart from one another, thereby preventing electrical contact between the first and second electrically conducting layers carried by the top and bottom portions 20t, 20b. The spacer layer can also function as a double-sided adhesive to adhere the top and bottom portions 20t, 20b to one another, as well as to secure the electrochemical module 30 to the carrier. The spacer layer can be formed from a variety of materials, including a material with adhesive properties, or the spacer layer can include a separate adhesive used to attach the spacer to the carrier and optionally to the electrochemical module. Non-limiting examples of ways in which adhesives can be incorporated into the various test strip assemblies of the present disclosure can be found in U.S. patent application Ser. No. 12/570,268 of Chatelier et al., entitled "Adhesive Compositions for Use in an Immunosensor" and filed on Sep. 30, 2009, the contents of which is incorporated by reference in its entirety.

The spacer layer can have various shapes and sizes, and it can be positioned on various portions of the carrier 20. In the embodiment shown in FIG. 1B, a spacer layer 28 is positioned on one side of the fold line 22 and extends over a substantial portion of the inwardly facing surface of the bottom portion 20b of the carrier 20. The spacer layer 28 can terminate at or just prior to the opening 24, so as to prevent the spacer layer 28 from extending into the opening 24 and from contacting the electrochemical module when the carrier 20 is folded. Termination at the opening 24, however, can facilitate the formation of a seal around the edge of the carrier adjacent to the opening 24. The spacer layer 28 can also terminate a distance from the second terminal end 21b of carrier 20 so that, when the carrier is folded as shown in FIG. 1D, the exposed portion of the inwardly facing surface of the bottom portion 20b is free from any adhesive material.

In another embodiment, shown in FIG. 1C, a spacer layer 29 is likewise positioned to cover a substantial portion of the inwardly facing surface of the bottom portion 20b. In this embodiment, however, the spacer layer 29 includes an extension portion 29a that extends toward or up to the fold line 22 adjacent to only one of the sidewalls, e.g., the first sidewall 21c. In other words, the extension portion 29a extends along only one side of the opening 24. The extension portion 29a of the spacer layer 29 will thus be positioned between the electrochemical module, e.g., module 30, and the carrier 20 to attach the electrochemical module 30 to the carrier 20 when the carrier is folded. Preferably, the extension portion 29a is positioned to contact an exterior surface, e.g., the bottom exterior surface, of the electrochemical module 30, and not one of the inwardly facing surfaces as will be discussed below. Optionally, the spacer layer 29 can also include a separate portion 29b that is positioned on a side of the opening 24 opposite to the extension portion 29a, and that is also positioned on an opposite side of the fold line 22. This separate portion 29b will thus contact the opposite exterior surface, e.g., the top exterior surface, of the electrochemical module 30, as will be discussed below. A person skilled in the art will appreciate that the location of the spacer layer can vary.

In other aspects, the spacer layer 29 can be configured to have a size and shape that reduces fouling of punching/cutting tools with the adhesive. For example, the edge of the adhesive can be spaced a small distance (e.g., 0.5 mm) from the hole 24 to prevent a punch tool used to form the hole from coming into contact with the adhesive. Moreover, if the adhesive is printed, the edge of the adhesive can be spaced a small distance (e.g., 0.5 mm) from the sidewalls 21c, 21d to prevent a cutting tool from coming into contact with the adhesive during a singulation step (i.e., when multiple strips are cut to form singular strips).

The carrier 20 can also include electrical contacts for coupling to an analyte measurement device. The electrical contacts can be located anywhere on the carrier 20. In the illustrated embodiment, the second terminal end 21b of the carrier 20 includes first and second contacts 12, 14 configured to establish a connection between first and second electrodes, respectively, on the module 30 (discussed below) and an analyte measurement device. As best shown in FIG. 1D, the first contact 12 is in the form of first and second tabs 12a, 12b located on the terminal end 21b of the bottom portion 20b of the carrier 20. When the carrier is folded, the tabs 12a, 12b will extend a distance beyond the terminal end 21a of the top portion 20t of the carrier 20, as shown in FIG. 1D. The tabs 12a, 12b can be formed by a cut-out or u-shaped notch 16 extending into the second terminal end 21b of the bottom portion 20b of the carrier 20 at a substantial mid-portion thereof. The cut-out 16 is also effective to expose the first electrically conducting layer on the inwardly facing surface of the top portion 20t of the carrier 20, thereby forming the second contact 14 (shown in phantom in FIG. 1D) for connecting the first electrically conducting layer to an analyte measurement device. A person skilled in the art will appreciate that the electrical contacts can have a variety of configurations other than those illustrated. For example, U.S. Pat. No. 6,379,513, which is hereby incorporated by reference in its entirety, discloses another embodiment of an electrochemical cell connection means.

The configuration of the electrically contacts can allow a measurement device to recognize a test strip by sensing a decrease in resistance between the meter tangs that connect to the tabs 12a, 12b on the carrier, as shown in FIG. 1D. As a further feature, tab 14 in FIG. 1D can be made to have a width that allows two additional meter tangs to electrically connect to the tab 14. This allows the meter to ensure that sufficient electrical contact is made with tab 14 before the user is prompted to apply a liquid sample to the cavity 42 in the electrochemical module 30. Such a configuration can prevent a "waiting for sample" error which can be seen in systems which do not ensure good electrical contact prior to initiating an electrochemical assay. In another embodiment, where tab 14 does not have a width sufficient to connect with two meter tangs, electrical contact between the meter and tab 14 can still be monitored by performing a "dry capacitance" measurement before the liquid sample is applied to the electrochemical cavity 42. The capacitance measurement must fall within the range expected for a dry strip before the user is prompted to apply the liquid sample to the cavity 42 in the electrochemical module 30.

The carrier can be configured to couple to a variety of analyte measurement devices having various configurations. In general, the measurement device can include a processor, which may include one or more control units configured for performing calculations capable of calculating a correction factor in view of at least one measured or calculated parameter as well as configured for data sorting and/or storage. The microprocessor can be in the form of a mixed signal microprocessor (MSP) such as, for example, a member of the Texas Instruments MSP 430 family. In addition, the microprocessor can include volatile and non-volatile memory. In another embodiment, many of the electronic components can be integrated with the microcontroller in the form of an application specific integrated circuit.

The dimensions of the carrier can vary significantly depending on the configuration of the analyte measurement device, as well as the quantity and configuration of the electrochemical module(s) on the test strip assembly. In the embodiment shown in FIG. 1A, and by way of non-limiting example, the carrier 20 can have a width $W_c$ that is in the range of about 0 mm to 4 mm larger than the width of the electrochemical module. For example, the width $W_c$ of the carrier 20 can be in the range of about 5 mm to 50 mm. Also by way of non-limiting example, the carrier 20 can have a length $L_c$ in the unfolded configuration that is in the range of about 20 mm to 200 mm, and more preferably 30 mm to 50 mm. The dimensions of the opening(s) in the carrier 20 can also vary, but in an exemplary embodiment the opening 24 has a generally oval or rectangular configuration with a width $W_o$ as measured in a direction extending between the opposed sidewalls 21c, 21d that is in the range of about 3 mm to 49 mm. The length $L_o$ (in the unfolded configuration) of the opening can be in the range of about 0 to 6 mm larger than twice the length of the electrochemical module (the factor of two is required since the carrier web will be folded). For example, the length $L_o$ of the opening can be in the range of about 3 to 30 mm. When the carrier 20 is folded as shown in FIG. 1D, the opening 24 will have a depth $D_o$ that is one half of the length $L_o$, as measured from the fold line 22 inward. A person skilled in the art will appreciate that the terms "about" and "approximately" as used herein for any numerical values or ranges indicate a suitable dimensional tolerance that allows the part or collection of components to function for its intended purpose as described herein.

Electrochemical Module

The electrochemical module (ECM) can also have a variety of configurations and various electrochemical cell sensors known in the art can be used. In one embodiment, the module can include multiple electrodes and a reagent layer, and the module can be configured to receive and react with an analyte in a fluid sample. The multiple electrodes can be configured in any suitable configuration, such as adjacent one another and in the same plane, or facing one another in an opposed spaced apart relationship. The module can be mounted onto a carrier, such as carrier 20, such that the carrier serves as a support for the module and facilitates handling. As indicated above, the carrier can also electrically couple the module to an analyte measurement device.

Figure 2A:
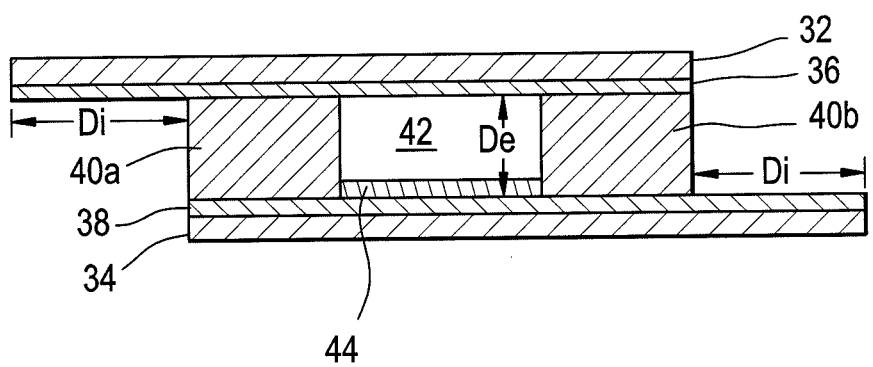
FIG. 2A is a side view of the ECM of FIG. 1B.
Figure 2B:
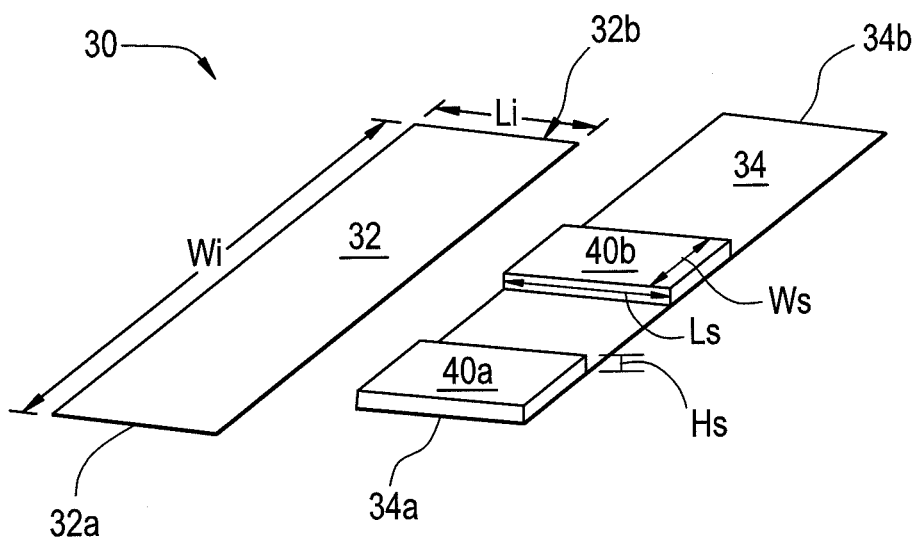
FIG. 2B is an exploded view of the ECM of FIG. 2A.

While the module can have various configurations, in the embodiment shown in FIGS. 2A-2B, the electrochemical module 30 generally includes a first insulating layer 32 carrying a first electrode 36, a second insulating layer 34 carrying a second electrode 38 that is in facing relationship with the first electrode 36 on the first insulating layer 32, and one or more spacers 40a, 40b maintaining the first and second electrodes 36, 38 at a distance apart from one another to define a cavity or chamber 42 therebetween for receiving a fluid analyte. For ease of reference, the first insulating layer 32 is also referred to herein as the top insulating layer, and the second insulating layer 34 is also referred to as the bottom insulating layer. The terms "top" and "bottom" are merely used to describe the illustrated orientation and are not intended to limit the layers to a particular orientation. The illustrated electrochemical module 30 can also include a reagent 44 disposed on one of the first and second electrodes, e.g., the second electrode 38, and disposed between the spacers 40a, 40b and within the chamber 42 for reacting with an analyte. A person skilled in the art will appreciate that the electrochemical module 30 can have a variety of configurations, including having other electrode configurations, such as co-planar electrodes.

The first and second insulating layers 32, 34 can each have various shapes and sizes, and the particular configuration of the insulating layers 32, 34 can vary depending on the particular configuration of the carrier 20. In the illustrated embodiment, the first and second insulating layers 32, 34 each have a generally rectangular shape. The insulating layers 32, 34 can be formed from various materials, but in an exemplary embodiment the insulating layers 32, 34 are formed from a material having a small coefficient of thermal expansion such that the insulating layers 32, 34 do not adversely affect the volume of the reaction chamber 42, as will be discussed in detail below. In one exemplary embodiment, at least one of the insulating layers, e.g., the first layer 32, can be formed from a transparent material to allow visualization of fluid flow into the reaction chamber. Suitable materials include, by way of non-limiting example, plastics (such as PET, PETG, polyimide, polycarbonate, polystyrene), ceramic, glass, adhesives.

As indicated above, each insulating layer 32, 34 can carry an electrode 36, 38. As shown in FIG. 2A, an inwardly facing surface of the first insulating layer 32 carries the first electrode 36, and an opposing inwardly facing surface of the second insulating layer 34 carries the second electrode 38. The electrodes 36, 38 can each be formed from a layer of conductive material, such as gold, palladium, carbon, silver, platinum, tin oxide, iridium, indium, and combinations thereof (e.g., indium doped tin oxide). Carbon in the form of graphene may also be used. The conductive material can be deposited onto the insulating layers 32, 34 by various processes, such as sputtering, electroless plating, thermal evaporation and screen printing. In an exemplary embodiment, the reagent-free electrode, e.g., the first electrode 36, is a sputtered gold electrode, and the electrode containing the reagent 44, e.g., the second electrode 38, is a sputtered palladium electrode. As discussed in further detail below, in use one of the electrodes can function as a working electrode and the other electrode can function as the counter/reference electrode.

When the electrochemical module 30 is assembled, the first and second insulating layers 32, 34, and thus the first and second electrodes 36, 38, can be held together at a spaced distance apart by one or more spacers. As shown in FIG. 2B, the electrochemical module 30 includes first and second spacers 40a, 40b, also referred to as adhesives. The illustrated spacers 40a, 40b each have a generally rectangular configuration with a length $L_s$ that can be substantially equal to a length $L_i$ of the insulating layers 32, 34, and a width $W_s$ that is significantly less than a width $W_i$ of the insulating layers 32, 34. However, the shape and size, as well as the quantity, of the spacers 40a, 40b can vary significantly. As shown, the first spacer 40a is positioned adjacent to a first terminal end 34a of the second/bottom insulating layer 34, and the second spacer 40b is positioned near a mid-portion of the second/bottom insulating layer 34 such that a space or gap is defined between the first and second spacers 40a, 40b. The second terminal end 32b of the first/top insulating layer 32 can be positioned in substantial alignment with an edge of the second spacer 40b farthest from the first spacer 40a, such that the first terminal end 32a of the first/top insulating layer 32 extends a distance beyond the first terminal end 34a of the second/bottom insulating layer 34. As a result, the second terminal end 34b of the second/bottom insulating layer 34 will extend a distance $D_i$ beyond the second terminal end 32b of the first/top insulating layer 32, as shown in FIG. 2A. The first and second insulating layers 32, 34 can thus be positioned offset from one another, thereby exposing an inwardly facing portion of each of the first and second electrodes 36, 38. A person skilled in the art will appreciate that the particular configuration, including the shape, orientation, and location of the spacer(s) and the insulating layers relative to one another can vary.

As indicated above, the spacers 40a, 40b and electrodes 36, 38 define a space or gap, also referred to as a window, therebetween which forms an electrochemical cavity or reaction chamber 42 for receiving a fluid sample. In particular, the first and second electrodes 36, 38 define the top and bottom of the reaction chamber 42, and the spacers 40a, 40b define the sides of the reaction chamber 42. The gap between the spacers 40a, 40b will result in the opposed sidewalls of the module 30 having openings or inlets extending into the reaction chamber 42. The fluid sample can thus be loaded through the side openings.

As further shown in FIG. 2A, the reaction chamber 42 can also include a reagent 44 disposed on at least one of the electrodes, e.g., the second electrode 38. Alternatively, the reagent layer can be disposed on multiple faces of the reaction chamber 42. The reagent 44 can be formed from various materials, including various mediators and/or enzymes. Suitable mediators include, by way of non-limiting example, ferricyanide, ferrocene, ferrocene derivatives, osmium bipyridyl complexes, and quinone derivatives. Suitable enzymes include, by way of non-limiting example, glucose oxidase, glucose dehydrogenase (GDH) based on pyrroloquinoline quinone (PQQ) co-factor, GDH based on nicotinamide adenine dinucleotide co-factor, and FAD-based GDH [E.C.1.1.99.10]. One exemplary reagent formulation, which would be suitable for making the reagent 44, is described in pending U.S. Pat. No. 7,291,256, entitled "Method of Manufacturing a Sterilized and Calibrated Biosensor-Based Medical Device," the entirety of which is hereby incorporated herein by reference. The reagent 44 can be formed using various processes, such as slot coating, dispensing from the end of a tube, ink jetting, and screen printing. Such processes are described, for example, in the following U.S. patents, which are hereby incorporated by reference in their entireties: U.S. Pat. Nos. 6,749,887; 6,869,441; 6,676,995; and 6,830,934. While not discussed in detail, a person skilled in the art will also appreciate that the various electrochemical modules disclosed herein can also contain a buffer, a wetting agent, and/or a stabilizer for the biochemical component.

The size of the electrochemical module 30 and its components can vary. For example, in one embodiment, the first and second insulating layers 32, 34 can each have substantially the same size, with a length $L_i$ and width $W_i$ that is less than a length $L_c$ and width $W_c$ of the carrier 20. By way of non-limiting example, the insulating layers 32, 34 can each have a width $W_i$ that is at least twice the length $L_i$. For example, the width $W_i$ can be in the range of about 3 mm to 48 mm, and more preferably about 6 mm to 10 mm, and a length $L_i$ in the range of about 0.5 mm to 20 mm, and more preferably 1 mm to 4 mm. The distance $D_e$ between the top electrode 36 and the bottom electrode 38, as well as the dimensions of the spacers 40a, 40b, can also vary depending on the desired volume of the reaction chamber 42. In an exemplary embodiment, the reaction chamber 42 has a small volume. For example, the volume can range from about 0.1 microliters to about 5 microliters, preferably about 0.2 microliters to about 3 microliters, and more preferably about 0.2 microliters to about 0.4 microliter. To provide the small volume, the gap between the spacers 40a, 40b can have an area ranging from about 0.005 cm$^2$ to about 0.2 cm$^2$, preferably about 0.0075 cm$^2$ to about 0.15 cm$^2$, and more preferably about 0.01 cm$^2$ to about 0.08 cm$^2$, and the thickness of the spacers 40a, 40b (i.e., the height $H_s$) can range from about 1 micron to 500 microns, and more preferably about 10 microns to 400 microns, and more preferably about 40 micros to 200 micros, and even more preferably about 50 microns to 150 microns. As will be appreciated by those skilled in the art, the volume of the reaction chamber 42, the area of the gap between the spacers 40a, 40b, and the distance between the electrodes 36, 38 can vary significantly.

Test Strip Assembly

Various techniques can be used to prepare a test strip assembly having both a carrier and an electrochemical module. Referring back to FIGS. 1A-1D, in one embodiment a single test strip assembly 10 can be formed by providing a carrier, e.g., carrier 20, and placing a spacer layer 28 or 29 and an electrochemical module 30 onto the carrier 20. The electrochemical module 30 is preferably mounted onto the carrier 20 in such a way as to allow the carrier 20 to function as a support for handling the apparatus, while also allowing easy access to the reaction chamber 42. While the particular location of the module 30 relative to the carrier 20 can vary depending on the configuration of the module 30, the quantity of modules 30 mounted onto the carrier 20, and the configuration of the carrier 20, in the illustrated embodiment the module 30 is mounted on the carrier 20 such that the module 30 extends across the opening 24 and is positioned along or adjacent to one side of the fold line 22. The opposed terminal ends of the module 30 are thus in contact with the carrier 20, while a central or mid-portion of the module 30 is not in contact with and is spaced apart from the carrier 20. The spacer layer 28 or 29 can likewise be positioned at various locations on the carrier 20. As explained above, the spacer layer 28 or 29 can function as an adhesive to secure the module 30 between the top and bottom portions 20t, 20b of the carrier 20, thus preventing movement of the module 30 relative to the carrier 20. While FIG. 1B illustrates the spacer 28 positioned a distance apart from the module 30 such that the spacer 28 does not contact the module 30 even when the carrier 20 is folded, the spacer can have other configurations such as the configuration shown in FIG. 1C in which the spacer 29 has portions 29a, 29b that extend over at least the terminal end portions of the module 30 to adhere the module 30 directly to the carrier 20.

Once the module 30 and spacer 28 or 29 are positioned on the carrier 20, the carrier 20 can be folded along the fold line 22, as shown in FIG. 1D, thereby adhering the top and bottom portions 20t, 20b to one another and thereby engaging the electrochemical module 30 between the top and bottom portions 20t, 20b. When folded, the carrier 20 will have a proximal end 20p with the first and second electrical contacts 12, 14, and a distal end 20d having the module 30 located thereon. The module 30 can be positioned adjacent to or along the terminal distal edge or perimeter of the carrier 20 such that one side of the opening extending into the reaction chamber 42 is positioned along the perimeter to allow for side loading of a fluid sample into the reaction chamber 42. The other side of the module 30, e.g., the proximal side, is spaced a distance apart from the inner edge of the opening 24 to create a gap. The gap between the carrier and the module allows a fluid sample to flow into the reaction chamber 42 without flowing into the carrier 20, e.g., between the top and bottom portions 20t, 20b. As used herein, the term "proximal" indicates that a reference structure is close to the test meter and the term "distal" indicates that a reference structure is farther away from the test meter.

When fully assembled, as shown in FIG. 1D, the inwardly facing surface of the top electrode 36 will directly contact and electrically connect with the inwardly facing surface of the bottom portion 20b of the carrier 20, and the inwardly facing surface of the bottom electrode 38 will directly contact and electrically connect with the inwardly facing surface of the top portion 20t of the carrier 20. The connection results from the offset configuration of the insulating layers 32, 34 and electrodes 36, 38, as shown in FIG. 2A. In particular, FIG. 2B shows that the connection will occur at the first terminal end 32a of the first/top insulating layer 32 that extends a distance beyond the first terminal end 34a of the second/bottom insulating layer 34, and at the second terminal end 34b of the second/bottom insulating layer 34 that extends a distance beyond the second terminal end 32b of the first/top insulating layer 32. The first electrode 36 is shielded from contacting the top portion 20t of the carrier 20 by the first insulating layer 32, and the second electrode 38 is shielded from contacting the bottom portion 20b of the carrier by the second insulating layer 34. The first electrode 36 will therefore communicate with an analyte measurement device through the bottom portion 20b of the carrier and through the first electrical contact 12, e.g., tabs 12a and 12b, and the second electrode 38 will communicate with the analyte measurement device through the top portion 20t of the carrier and through the second electrical contact 14. The spacer layer will maintain electrical separation between the top and bottom portions 20t, 20b of the carrier 20.

The assembled dimensions of the ECM and the test strip assembly can vary, but in one exemplary embodiment the ECM has a width of about 10 mm and a length (measured in a proximal-distal direction) of about 2 mm, and the carrier or test strip assembly has a width of about 12 mm and a length (measured proximal-distal direction) of about 40 mm. The dimensions of the carrier are thus significantly larger than the dimensions of the ECM.

Exemplary Manufacturing Process

In one exemplary embodiment, a test strip assembly can be manufactured by applying a coating of conducting carbon ink to a 76 mm wide web of glossy cardboard, PET or polypropylene having an appropriate stiffness. The thickness of the coating should be sufficient to reduce the surface resistance such that the overall resistance of the connector track is less than 200 Ohms. The conducting layer on the carrier can be etched downweb with a laser or a mechanical scriber at a location 40 mm from one edge such that the web is divided into two electrically isolated functional regions, e.g., top portion 20t and bottom portion 20b. For a carrier web having multiple test strip assemblies, e.g., a multi-panel test strip assembly, the web can also be etched in a crossweb direction at 20 mm intervals to separate each test strip assembly. A spacer or adhesive layer, e.g., spacer 128, covered by a release liner can be laminated to the web, as shown in FIG. 3C, such that one of its edges is 4 mm from the terminal end of the bottom portion 20b of the carrier web and the other edge is about 5 mm above the center line of the carrier web. Referring back to FIG. 3C, note that the center line can correspond to the location of the fold line 122. Holes 124, having a diameter of 8 mm, can be punched into the carrier web in a downweb direction along the etched line at 12 mm intervals (center-to-center), and slots can be punched in the bottom (proximal) end. For a multi-panel test strip assembly, the holes can be in the middle of each 20 mm section. A 34 mm wide track of double-sided adhesive separator (about 95±2 micrometers height with 50 micrometer release liners) can be kiss-cut and the waste removed in such a way that there are 4 repeating patterns, shown in part in FIG. 8, which consist of (1) a 1.2 mm wide cavity (labeled "a" in FIG. 8) in the middle that will form an electrochemical cavity in a later step, and (2) a 2.4 mm wide spacer section separator (labeled "b" in FIG. 8) on each side that will form the walls of the electrochemical cavity in a further step. The term kiss-cut can be used when referring to a partial cut through a laminate structure. For example, the laminate structure including an Au-PET layer, an adhesive spacer layer, and a Pd-PET layer can be kiss-cut such that only the Au-PET layer or Pd-PET layer is cut. The remaining separator will form a reagent-free cavity (2 mm on each side, labeled "c" in FIG. 8) that will expose overhanging electrodes in a further step. A 32 mm wide track of PET filled with barium sulfate particles is sputtered with 60 nm of Pd, brought into contact with 0.3 mM MESA in water for 20 seconds, and then the excess liquid is blown off with an air knife. Four strips of reagent (identical or different) are applied to the Pd electrode, 8 mm apart (center-to-center). The double-sided adhesive separator is bonded to the Pd electrode in such a way that each 1.2 mm wide cavity overlays a reagent stripe. A 32 mm wide track of clear PET is sputtered with 30 nm of Au, brought into contact with 0.3 mM MESA in water for 20 seconds, and then the excess liquid is blown off with an air knife. The Pd-separator-Au tri-laminate is kiss-cut through the electrode layer only from two directions, as shown by the arrows in FIG. 8, in such a way that either the Pd or the Au extends past the edge of the spacer layer and the other electrode layer. The different tracks of tri-laminate can be separated to form four electrochemical modules, two of which are shown in FIG. 8 and labeled A and B, with only a portion of the remaining two being shown. The total width of each of the modules will be 2 mm (section c, upper electrode)+2.4 mm (section b, trilaminate)+1.2 mm (section a, cavity plus reagent)+2.4 mm (section b, trilaminate)+2 mm (section c, lower electrode), for a total of 10 mm. This is larger than the total length of 32 divided by 4 (about 8 mm) because of the separate exposed regions of upper and lower electrodes. Each module of tri-laminate is cut into 2 mm long sensors and placed on the carrier as described above. One way to achieve this is to push a leading edge of the tri-laminate into a slot on a wheel and cut off the 2 mm wide sensor. The wheel would then rotate so that another slot would receive the leading edge of the tri-laminate web and another piece of 2 mm wide sensor would be cut off, etc. The carrier web would advance past the opposite end of the wheel and receive each 2 mm wide sensor in such a way that the appropriate edge of the electrochemical cavity coincides with the middle of a hole in the carrier. For the multi-analyte test strip assembly, the track order along the carrier would be 1-2-3-4, 1-2-3-4, etc., with a separate rotating wheel for each reagent. Since each small ECM is 10 mm wide and each carrier is 12 mm wide, there will be sufficient gap between each edge of the ECM and carrier so that the cutting machine does not disturb the ECM in the final "singulation" step. The carrier is folded at a line which was laser etched downweb, bonded to the double sided adhesive separator, optionally printed with a logo and other required information, and then chopped as appropriate. The folding process can either be done continuously in a web process, or the web can be chopped into cards which can then be folded. For the multi-analyte test strip assembly, a set of four ECMs can be chopped into a single card. If all reagents are identical and an average value is required, then each card can contain two or four ECMs. Alternatively, the web can be processed for the simplest application with single, identical sensors.

Other Embodiments

While one embodiment of a test strip assembly 10 is shown in FIG. 1D, FIGS. 3A-4 provides various other embodiments of test strip assemblies. A person skilled in the art will appreciate that, while not specifically discussed, the test strip assemblies set forth in FIGS. 3A-4 can include any combination of features discussed above with respect to FIGS. 1A-1D and/or other features known in the art.

In one embodiment, a carrier web having multiple test strips assemblies can be formed. Such a configuration allows for mass production of multiple test strip assemblies. Each test strip assembly can simply be cut or otherwise removed from the carrier web prior to use. For example, the carrier web can include scored regions between each test strip assembly to facilitate removal of a test strip assembly without the need for scissors or another cutting mechanism. Alternatively, an analyte measurement device can have multiple terminals configured to accept a carrier web having multiple electrochemical modules. Such a configuration could allow for multiple analytes to be tested simultaneously. Such a configuration could, in other embodiments, allow multiple readings of a single analyte to be taken, thus allowing the device to exclude outliers and display an average. This would provide a robust estimate of the analyte concentration and can enhance both the precision and the accuracy of the measurement.

Figure 3A:
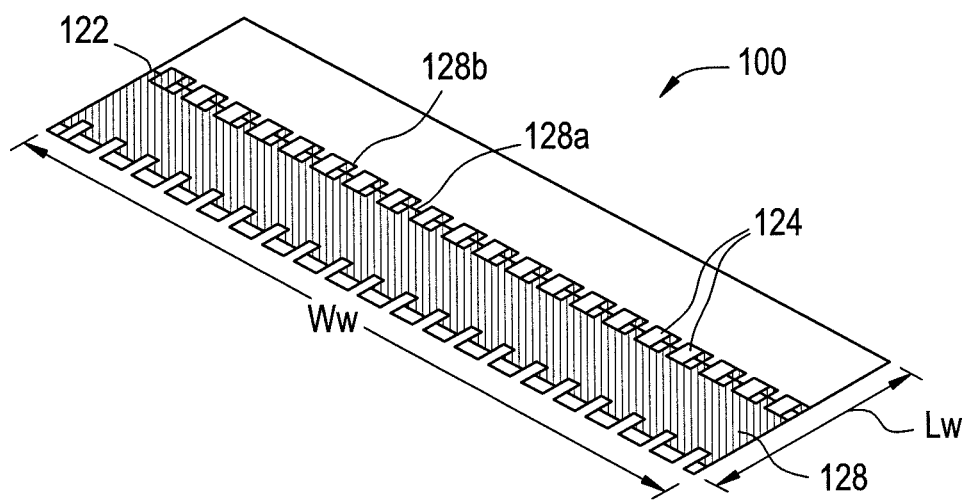
FIG. 3A is a perspective view of a carrier web shown in an unfolded configuration and having an adhesive disposed thereon, the carrier web forming multiple carriers for forming multiple test strip assemblies.

While the carrier web can have various configurations, FIG. 3A illustrates one embodiment of a carrier web 100 having a generally elongate rectangular configuration. The carrier web 100 can have the same length $L_w$ as the length $L_c$ of the carrier 20 discussed above with respect to FIG. 1A, however the width $W_w$ of the carrier web 100 can be multiple times the width $W_c$ of the carrier 20 discussed with respect to FIG. 1A. In particular, the width $W_w$ of the carrier web 100 preferably corresponds to the width $W_c$ of the carrier of FIG. 1A times the number of carriers that the carrier web 100 is to contain. For example, if the carrier web 100 is configured to produce ten (10) carriers, and thus ten test strip assemblies, then the width $W_w$ of the carrier web 100 will be about ten (10) times the width $W_c$ of a single carrier. A person skilled in the art will appreciate that the particular dimensions of the carrier web 100 can vary.

Figure 3B:
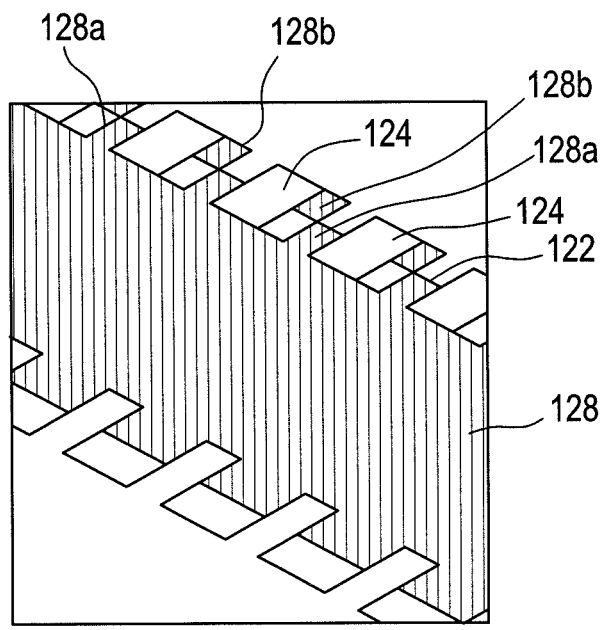
FIG. 3B is an enlarged perspective view of a portion of the carrier web and adhesive shown in FIG. 3A.
Figure 3C:
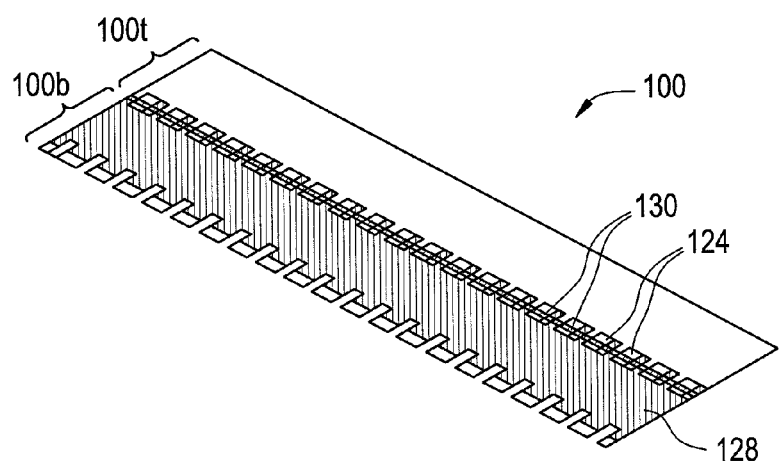
FIG. 3C is perspective view of the carrier web and adhesive of FIG. 3A having an ECM disposed across each opening in the carrier web.
Figure 3D:
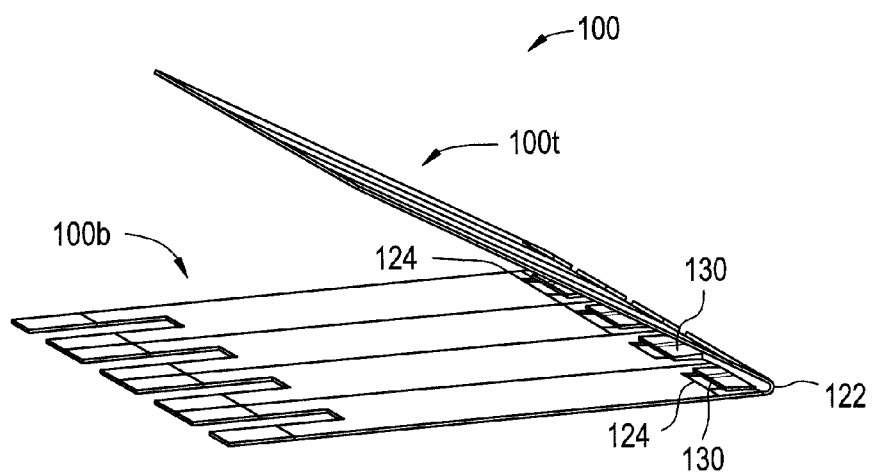
FIG. 3D is a perspective view of the carrier web, adhesive, and ECMs of FIG. 3B shown partially folded.

As further shown in FIGS. 3A and 3B, the carrier web 100 can include multiple openings 124 formed therein, each opening 124 having a configuration similar to the openings 24 previously discussed above with respect to FIG. 1A. As shown, the openings 124 can be spaced a distance apart from one another and longitudinally aligned along an intended fold line 122 on the carrier web 100. The carrier web 100 can also include an adhesive or spacer 128 disposed on various portions of the carrier web 100. In the illustrated embodiment, the spacer 128 is positioned on one side of the intended fold line 122. The spacer 128 can include a portion 128a that extends along one side of each opening 124 for contacting a bottom surface of the electrochemical module, e.g., module 130, when mounted thereon. The spacer 128 can also include a separate, second portion 128b that is positioned on an opposite side of each opening 124, and on an opposite side of the fold line 122 such that the second portion 128b of spacer 128 contacts a top surface of the electrochemical module 130. When the carrier web 100 is folded, the spacer 128 will connect the top and bottom portions of the carrier web 100 to one another, while maintaining the top and bottom portions 100t, 100b at a spaced apart distance from one another. The portions of spacer 128 that extend along each side of the openings 124 will adhere to and affix each electrochemical module 130 to the carrier web 100, thereby maintaining the modules 130 in a fixed position relative to the carrier web 100.

FIG. 3C illustrates the carrier web 100 of FIGS. 3A and 3B having an electrochemical module 130 mounted to extend across each opening 124 in the web. Each module 130 on the web 100 can have a configuration as previously explained. In other embodiments, the modules 130 on the carrier web 100 can differ from one another, e.g., to allow different analytes to be tested. A person skilled in the art will appreciate that the configuration of the carrier web 100 and modules 130 mounted thereon, as well as the location of each module 130 on the carrier web 100, can vary significantly depending on the intended use.

FIG. 4A illustrates another embodiment of an electrochemical module 230, and FIG. 4B illustrates the electrochemical module mounted 230 onto a carrier 220 to form a test strip assembly 200. In this embodiment, the electrochemical module 230 has a curved or bent configuration to position the electrochemical cell or reaction chamber 242 a farther distance apart from the inner edge of the opening 224 in the carrier 220. In particular, the electrochemical module 230 has a configuration similar to that described above with respect to FIGS. 2A and 2B, however the module 230 includes bent or angled end portions. As shown, a portion of the module 230 which contains the reaction chamber 242, e.g., a mid-portion 230a, extends along a central axis $L_1$, and two terminal end portions 230b, 230c each extend along axes $L_2$, $L_3$ that extend at an angle α relative to the central axis $L_1$ of the mid-portion 230a. The central axis $L_1$ can also extend orthogonal to a direction of flow of a sample into the reaction chamber 242. The angle α between each end portion 230b, 230c and the mid-portion 230a can vary. For example, in the illustrated embodiment the angle α is an acute angle, and more particularly is greater than 0 degrees and less than 90 degrees. For example, the angle α can be about 45 degrees. Each terminal end portion 230b, 230c is preferably oriented to extend away from the central axis $L_1$ of the mid-portion 230a in the same direction. Such a configuration allows the terminal end portions 230b, 230c to be mounted onto the carrier 220 on opposed sides of the opening 242, as shown in FIG. 4B, with the mid-portion 230a positioned a distance apart from the inner edge of the opening 224. The distance d can vary depending on the length of the end portions 230b, 230c, but in an exemplary embodiment the electrochemical module 230 is configured such that the distal-most edge 230d of the module 230 is positioned distal to the distal-most edge 220d of the carrier 220. As a result, the distance d between the proximal edge of the module 230 and the proximal inner edge of the carrier 220 at the opening 224 is increased to help prevent fluid from flowing from the reaction chamber 242 into the carrier 220.

FIG. 5 illustrates multiple electrochemical modules 230, having the same configuration as the module of FIG. 4A, mounted onto a carrier web 300, similar to the carrier web 100 discussed above with respect to FIG. 3D. A person skilled in the art will appreciate that the web and the modules can have a variety of configurations, and can include any combination of features disclosed herein and/or known in the art.

Figure 6:
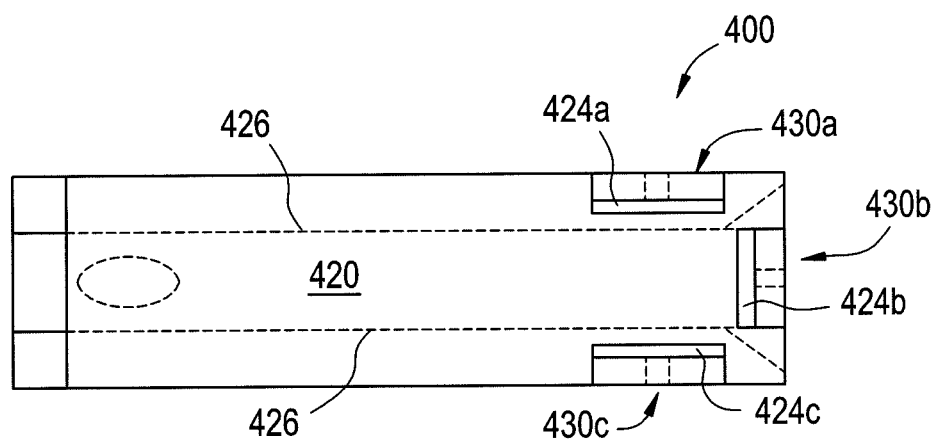
FIG. 6 is a top view of yet another embodiment of a test strip assembly having multiple ECMs.

FIG. 6 illustrates another embodiment of a test strip assembly 400, shown fully assembled in a folded configuration. In this embodiment, the assembly 400 includes multiple electrochemical modules 430a, 430b, 430c mounted at various locations on a single carrier 420. In particular, the carrier 420 has a configuration similar to the carrier 20 of FIG. 1A, however, in addition to the distal opening 424b, the carrier 420 includes first and second opposed side openings 424a, 424c extending through each of the top and bottom portions of the carrier 420. This allows three electrochemical modules 430a, 430b, 430c to be mounted onto the carrier 420 between the top and bottoms portions of the carrier 420. Each module 430a, 430b, 430c can be positioned to extend across an opening 424a, 424b, 424c, as shown. Each module 430a, 430b, 430c can be configured to measure the same analyte in a fluid sample, or to measure different analytes. Multiple electrical isolation lines or "breaks" 426 can be formed in the carrier to electrically isolate each module 430a, 430b, 430c and allow the carrier 420 to provide separate electrically connections between each module 430a, 430b, 430c and different electrical connections on an analyte measurement device. A person skilled in the art will appreciate that each module can have various configurations, including a configuration similar to the embodiment of FIG. 4A, and that the modules can be mounted at various locations on the carrier 420, or on a carrier web. The electrical contacts for coupling to an analyte measurement device can also have a variety of configurations.

Use

The test strip assemblies disclosed herein are suitable for use in the determination of a wide variety of analytes in a wide variety of samples, and are particularly suited for use in the determination of analytes in whole blood, plasma, serum, interstitial fluid, or derivatives thereof. By way of non-limiting example, the electrochemical modules can be configured as a glucose sensor, a lactate sensor based on lactate dehydrogenase, a lactate dehydrogenase sensor which includes lactate (to report on tissue damage), a ketone body sensor based on β-hydroxy-butyrate dehydrogenase, a cholesterol sensor based on cholesterol oxidase, a hemoglobin sensor which includes a cytolytic agent such as deoxycholate, and an immunosensor which contains an antibody and/or an antigen.

In use, a test strip assembly can be loaded into an analyte measurement device, such as a meter. An audible confirmation of connection can optionally be provided. The test meter will connect to the first and second electrical connections on the test strip assembly to form a complete circuit. An example is shown in FIG. 1D where contacts 12a and 12b can be used to recognize strip insertion into the meter. The test meter can measure the resistance or electrical continuity between the electrical contacts on the test strip assembly to determine whether the test strip is electrically connected to the test meter. The test meter can use a variety of sensors and circuits to determine when a test strip is properly positioned with respect to the test meter. In one embodiment, a circuit disposed in the test meter can apply a test potential and/or a current between first electrical contact and second electrical contact. Once the test meter recognizes that a test strip assembly has been inserted, the test meter turns on and initiates a fluid detection mode. In one embodiment, the fluid detection mode causes the test meter to apply a constant current of about 1 microampere between the first electrode and the second electrode. An example is shown in FIG. 1D where the flow of current between contact 14 and contact 12 can be used to detect fluid in the strip. Because the test strip assembly is initially dry, the test meter measures a maximum voltage, which is limited by the hardware within the test meter. The fluid sample, such as a physiological fluid or control solution, can be delivered to the sample reaction chamber 42 for electrochemical analysis via the opening until the fluid sample fills the sample reaction chamber. When the fluid sample bridges the gap between the first and second electrodes, the test meter will measure a decrease in measured voltage (e.g., as described in U.S. Pat. No. 6,193,873, the entirety of which is hereby incorporated by reference), which is below a pre-determined threshold causing the test meter to automatically initiate the analyte test, e.g., a glucose test.

It should be noted that the measured voltage may decrease below a pre-determined threshold when only a fraction of the sample reaction chamber has been filled. A method of automatically recognizing that a fluid was applied does not necessarily indicate that the sample reaction chamber has been completely filled, but can only confirm a presence of some amount of fluid in the sample reaction chamber. Once the test meter determines that a fluid has been applied to the test strip assembly, a short, but non-zero amount of time may still be required to allow the fluid to completely fill the sample reaction chamber. At this point, the meter can apply a series of electrical potentials, measure the electrical current versus time, and use an algorithm to calculate the concentration of analyte in the test liquid.

Figure 7:
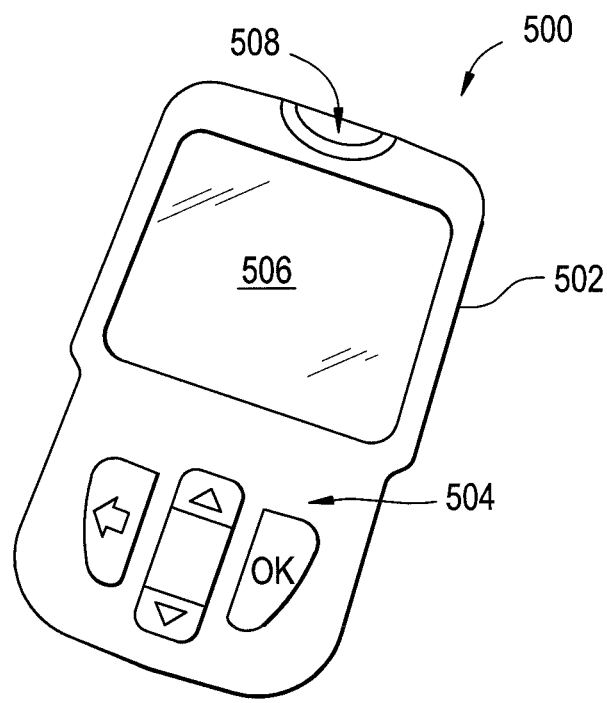
FIG. 7 is a top view of one embodiment of an analyte measurement device.

By way of non-limiting example, FIG. 7 illustrates one embodiment of an analyte measurement device, e.g., a diabetes management unit (DMU) 500. The DMU 500 generally includes a housing 502, user interface buttons 504, a display 506, and a test strip port opening 508. The user interface buttons 504 can be configured to allow the entry of data, navigation of menus, and execution of commands. Data can include values representative of analyte concentration, and/or information, which are related to the everyday lifestyle of an individual. Information, which is related to the everyday lifestyle, can include food intake, medication use, occurrence of health check-ups, and general health condition and exercise levels of an individual. The DMU can also be combined with an insulin delivery device, an additional analyte testing device, and/or a drug delivery device. The DMU may be connected to a computer or server via a cable or a suitable wireless technology such as, for example, GSM, CDMA, BlueTooth, WiFi and the like. A person skilled in the art will appreciate that the analyte measurement device can have a variety of configurations, and that various devices known in the art can be used. By way of non-limiting example, one exemplary embodiment of an analyte measurement device is disclosed in U.S. Publication No. 2009/0084687 entitled "Systems and Methods of Discriminating Control Solution From A Physiological Sample," which is hereby incorporated by reference in its entirety.

One skilled in the art will appreciate further features and advantages of the present disclosure based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A test strip configured for reception by a test meter, said test strip comprising:
   a carrier defined by one or more nonconductive substrates and having first and second electrically conductive regions that are electrically isolated from one another, the carrier including a fold line transverse to a major dimension of the carrier along which top and bottom portions are defined, said portions carrying the first and second conductive regions, respectively, and an opening extending therethrough; and
   an electrochemical module mounted to the carrier such that at least a portion of the electrochemical module extends across the opening and is thereby exposed, the electrochemical module having an electrochemical cavity with a first electrode in electrical communication with the first conductive region of the carrier, a second electrode in electrical communication with the second conductive region of the carrier, and a sample receiving chamber that includes a reagent layer and wherein the electrochemical module is mounted at opposing ends between the top and bottom portions within the opening.

2. The test strip of claim 1, wherein the opening extends across the fold line.

3. The test strip of claim 1, wherein the electrochemical module has a maximum length and a maximum width that is less than a maximum length and a maximum width of the carrier.

4. The test strip of claim 1, further comprising an adhesive disposed between the top and bottom portions of the carrier and configured to maintain the top and bottom portions at a fixed distance apart from one another.

5. The test strip of claim 1, wherein the sample receiving chamber of the electrochemical module is located between the opposed ends and is spaced apart from the carrier.

6. The test strip of claim 1, wherein the opening is located on a distal end of the carrier, and a proximal end of the carrier includes first and second contacts configured to establish a connection between the first and second electrodes and the test meter.

7. The test strip of claim 1, wherein the electrochemical module includes:
   a top insulating substrate carrying the first electrode;
   a bottom insulating substrate carrying the second electrode; and
   a spacer disposed between the first and second electrodes and maintaining the first and second electrodes in a spaced apart relationship with one another.

8. The test strip of claim 7, wherein the top and bottom insulating substrates are offset from one another such that a portion of the first electrode on the top insulating substrate is in contact with the second electrically conductive region on the carrier, and a portion of the second electrode on the bottom insulating substrate is in contact with the first electrically conductive region on the carrier.

9. The test strip of claim 1, wherein the electrochemical module has a central portion extending along a central axis and containing the electrochemical cavity, and opposed end portions having central axes that extend at an angle relative to the central axis of the central portion.

10. The test strip of claim 1, wherein the carrier is inert.

11. A test strip configured for reception by a test meter, said test strip comprising:

a carrier defined by one or more substrates made from a non-conducting material and having
a first conductive area defined on a top portion, and
a second conductive area defined on a bottom portion electrically isolated from the first conductive area, and an opening formed through the carrier and in which the top portion and the bottom portion of the carrier are defined by a fold line extending transverse to a major dimension of the carrier;
an electrochemical module mounted on the carrier such that at least a portion of the module extends across the opening in the carrier and is thereby exposed, the electrochemical module having
a first electrode in communication with the first conductive area of the carrier,
a second electrode in communication with the second conductive area of the carrier,
an electrochemical cavity for receiving a fluid sample, the electrochemical cavity being formed between the first and second electrodes, and
a reagent disposed within the electrochemical cavity on at least one of the first and second electrodes for reacting with an analyte of a fluid sample received in the electrochemical cavity in which the top portion carries the first conductive area and the bottom portion carries the second conductive area, and wherein the electrochemical module has opposed ends engaged between the top and bottom portions within the opening.

12. The test strip of claim 11, wherein the electrochemical module has a first insulating substrate carrying the first electrode, and a second insulating substrate carrying the second electrode, the first and second electrodes facing one another in a spaced apart relationship.

13. The test strip of claim 11, wherein the opening is located along a perimeter of the carrier.

14. The test strip of claim 11, wherein the carrier has a maximum length and maximum width that is greater than a maximum length and maximum width of the electrochemical module.

15. The test strip of claim 11, further comprising an adhesive disposed between the top and bottom portions of the carrier and configured to maintain the top and bottom portions at a fixed distance apart from one another.

16. The test strip of claim 11, wherein the first and second conductive regions on the carrier are electrically isolated from one another along the fold line.

17. The test strip of claim 11, wherein the opening is located along the fold line.

18. The test strip of claim 11, wherein the electrochemical module is located on a distal end of the carrier, and a proximal end of the carrier includes first and second contacts configured to establish a connection between the first and second electrodes and an analyte measurement device.

19. The test strip of claim 11, wherein the electrochemical module has a mid-portion located between the opposed ends and spaced a distance apart from the carrier.

20. The test strip of claim 11, wherein the electrochemical module has a central portion extending along a central axis and containing the electrochemical cavity, the opposed end portions having central axes that extend at an angle relative to the central axis of the central portion.

21. The test strip of claim 11, wherein the carrier is electrochemically non-functional.

22. A test strip configured for insertion within a test meter, said test strip comprising:
an electrochemical module having an electrochemical cavity with first and second electrodes, and a sample receiving chamber having a reagent layer configured to react with an analyte of a fluid sample received in the electrochemical cavity; and
a carrier having
a top insulating substrate having a first conductive region,
a bottom insulating substrate having a second conductive region,
a distal cut-out extending through a distal end of the top and bottom insulating substrates, at least a portion of the electrochemical module extending across the distal cut-out such that the first electrode is in electrical communication with the first conductive region and the second electrode is an electrical communication with the second conductive region, and
a proximal cut-out extending through a proximal end of the bottom insulating substrate of said carrier to expose a contact area on the first conductive region of the top insulating substrate such that the first contact area on the first conductive region of the top insulating substrate and a second contact area on the bottom insulating substrate are exposed to allow electrical connection with a test meter to establish a connection between the first and second electrodes and the test meter, the electrochemical module having opposed ends engaged between the top and bottom insulating substrates of the carrier at the distal cut-out, and wherein the electrochemical cavity is located between the opposed ends and extends outwardly away from the carrier.

23. A carrier web, comprising:
a carrier having first and second conductive areas electrically isolated from one another, and a plurality of openings spaced a distance apart from one another and disposed along a fold line; and
a plurality of electrochemical modules, each module being mounted across one of the plurality of openings and along the extending fold line, each electrochemical module having a first electrode in communication with the first conductive area, a second electrode isolated from the first electrode and in communication with the second conductive area, and an electrochemical cavity accessible through the opening in the carrier for receiving a fluid sample
wherein the fold line defines a top portion carrying the first conductive area and a bottom portion carrying the second conductive are;
and wherein the plurality of electrochemical modules are modules are mounted at opposing ends between the top and bottom portions within the openings.

* * * * *

UNITED STATES PATENT AND TRADEMARK OFFICE
CERTIFICATE OF CORRECTION

PATENT NO.        : 8,956,518 B2
APPLICATION NO.   : 13/090620
DATED             : February 17, 2015
INVENTOR(S)       : Garry Chambers et al.

It is certified that error appears in the above-identified patent and that said Letters Patent is hereby corrected as shown below:

In the Claims

Correct of Claim 23 is requested as follows:
Column 22
Line 54, 55, please change "conductive area and a bottom portion carrying the second conductive are;" to --conductive area and a bottom portion carrying the second conductive area;--
Line 57, please change "modules are mounted at opposing ends between the top" to --modules mounted at opposing ends between the top--

Signed and Sealed this
Ninth Day of June, 2015

Michelle K. Lee
*Director of the United States Patent and Trademark Office*